United States Patent [19]

Tulshian et al.

[11] Patent Number: 5,091,431
[45] Date of Patent: Feb. 25, 1992

[54] PHOSPHODIESTERASE INHIBITORS

[75] Inventors: Deen Tulshian, Rockaway; Ronald J. Doll, Maplewood, both of N.J.

[73] Assignee: Schering Corporation, Kenilworth, N.J.

[21] Appl. No.: 543,778

[22] PCT Filed: Feb. 6, 1989

[86] PCT No.: PCT/US89/00409

§ 371 Date: Jul. 18, 1990

§ 102(e) Date: Jul. 18, 1990

[87] PCT Pub. No.: WO89/07102

PCT Pub. Date: Aug. 10, 1989

Related U.S. Application Data

[63] Continuation-in-part of Ser. No. 153,114, Feb. 8, 1988, abandoned.

[51] Int. Cl.$^5$ .................. A61K 31/52; C07D 473/18; C07D 473/34; C07D 473/16
[52] U.S. Cl. .................. 514/262; 514/266; 544/264; 544/276; 544/277; 549/465; 558/44; 558/51; 560/119; 562/501
[58] Field of Search .............. 544/276, 277; 514/262, 514/266

[56] References Cited

U.S. PATENT DOCUMENTS

| | | | |
|---|---|---|---|
| 4,460,765 | 7/1984 | Naito et al. | 536/26 |
| 4,634,706 | 1/1987 | Kaneko et al. | 514/262 |
| 4,822,879 | 4/1989 | Nakagawa et al. | 544/277 |
| 4,971,972 | 11/1990 | Doll et al. | 544/277 X |

FOREIGN PATENT DOCUMENTS

| | | |
|---|---|---|
| 29329 | 5/1981 | European Pat. Off. |
| 44527 | 1/1982 | European Pat. Off. |
| 162715 | 11/1985 | European Pat. Off. |
| 214708 | 3/1987 | European Pat. Off. |
| 143557 | 6/1987 | European Pat. Off. |
| 60-149394 | 8/1985 | Japan |
| 61-100593 | 5/1986 | Japan |

OTHER PUBLICATIONS

F. Nakagawa et al., *J. Antibiotics*, 38 (7), (1985), pp. 823–829.
S. Takahashi et al., *J. Antibiotics*, 38 (7), (1985), pp. 830–834.
Marquez et al., *Med. Res. Rev.*, 6 (1), (1986), pp. 1–16 and 36–40.

*Primary Examiner*—Diana G. Rivers
*Attorney, Agent, or Firm*—Anita W. Magatti; James R. Nelson

[57] ABSTRACT

Compounds having an optionally-substituted purine derivative portion and a carbobicyclic or heterobicyclic portion, which compounds are useful as phosphodiesterase inhibitors, are disclosed. Also disclosed are intermediates, methods for making the inhibitors, pharmaceutical compositions and methods for treating hypertension using the compounds.

6 Claims, No Drawings

PHOSPHODIESTERASE INHIBITORS

This application claims priority of International application PCT/US89/00409, filed internationally on Feb. 6, 1989, which application is a continuation-in-part of Ser. No. 07/153,114, filed Feb. 8, 1988 now abandoned.

SUMMARY

The present invention relates to nucleoside-type compounds having an optionally substituted purine derivative as the base joined to a carbobicyclic or heterobicyclic moiety. Said compounds are useful as phosphodiesterase inhibitors, in particular as antihypertensives.

The present invention also relates to pharmaceutical compositions comprising said nucleoside-type compounds, methods of preparing said compounds and to a method of treating hypertension comprising administering said compound or composition to a mammal in need of such treatment.

BACKGROUND

Cyclic guanosine monophosphate (cGMP) is known to be an important physiological mediator of vasorelaxation. A major process in vascular smooth muscle contraction is hydrolysis of cGMP by calcium-calmodulin dependent phosphodiesterase (Ca CaM PDE). Since Ca CaM PDE is selective for cGMP, selective inhibition of this enzyme should elevate cGMP levels in vascular smooth muscle and induce vasorelaxation.

Griseolic acid, disclosed in U.S. Pat. No. 4,460,765, is a nucleoside-type compound having an adenine base and a bicyclic sugar moiety and has a structure similar to adenosine 3',5'-cyclic monophosphate (cAMP). cAMP is known to be a mediator of a large number of hormones and griseolic acid similarly appears to inhibit a large variety of phosphodiesterases (PDEs).

DETAILED DESCRIPTION

Compounds of the invention are represented by the formula

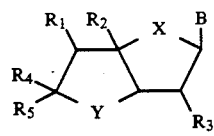

I wherein
$R_1$ is hydrogen or $R_1$ and $R_2$ together may form a double bond;
$R_2$ is hydrogen or $R_2$ may form a double bond with either $R_1$ or X;
$R_3$ is hydrogen or OH;
$R_4$ is hydrogen or $-(CH_2)_n COOR_6$;
$R_5$ is $R_4$ or $-CH(COOR_6)(CH_2COOR_6)$, provided that $R_4$ and $R_5$ are not both hydrogen;
$R_6$ is hydrogen or lower alkyl;
n is 0–4;
X is $-CH_2-$, $-NH-$, $-P-$ or when $R_1$ is hydrogen, X may be $-CH=$ and form a double bond with $R_2$;
Y is $-CH_2-$, $-NH-$, $-P-$, $-S-$ or $-O-$;
B is

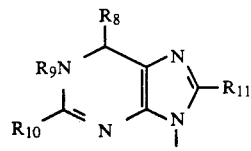

$R_8$ is $-OH$ or $-NH_2$;
$R_9$ is hydrogen, lower alkyl or aryl;
$R_{10}$ is hydrogen, amino, lower alkylamino, arylamino, lower alkylcarbonylamino, heteroaryl or heteroaryl substituted by 1-3 substituents independently selected from lower alkyl, amino, hydroxy, halogeno, thio, alkylthio and arylthio;
$R_{11}$ is hydrogen, halogeno, lower alkyl or aryl; and the pharmaceutically acceptable esters or salts thereof.

The present invention also is directed to a compound of claim 1 in combination with a pharmaceutically acceptable carrier.

The present invention further comprises the use of a compound of formula I for the preparation of a medicament for treating hypertension.

The present invention also is directed at a method for reducing blood pressure in hypertensive animals comprising administering to a mammal in need of such treatment an effective amount of a compound of formula I in combination with a pharmaceutically acceptable carrier.

The present invention also is directed at a process for producing a compound of formula I characterized by:
a. reacting a compound of formula Ia with a compound of formula Ba

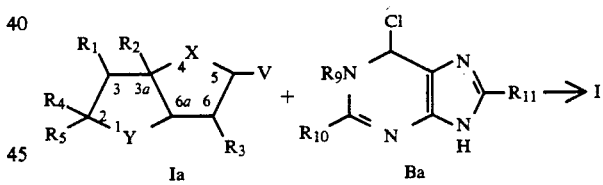

where V is methanesulfonyloxy, halogen or tosyl; or
b. reacting a compound of formula

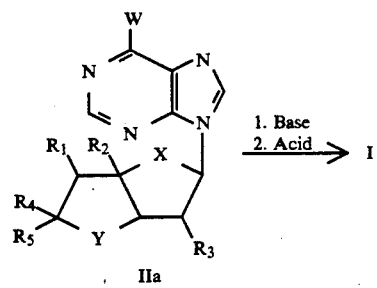

where W is chlorine, bromine, OR or NHR where R is a protecting group and the remaining substituents are as previously defined.

The present invention also is directed at intermediate compounds of the formulae

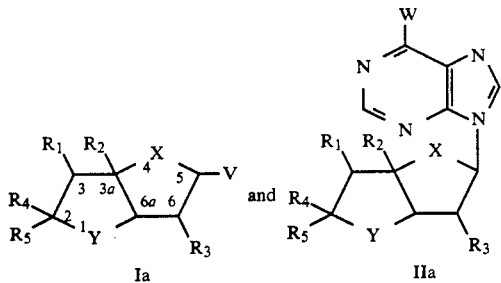

Ia and IIa where the substituents are as previously defined.

Those skilled in the art will recognize that tautomerism exists in group B, i.e.,

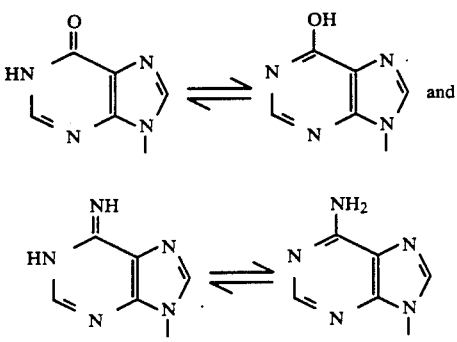

As used herein the term "lower alkyl" refers to straight or branched chain alkyl groups of 1-6 carbon atoms or cycloalkyl groups of 3-6 carbon atoms, e.g., methyl, ethyl, n-propyl, isopropyl, cyclopropyl, n-butyl, isobutyl, cyclobutyl, pentyl, hexyl and cyclohexyl.

The term "halogeno" refers to fluoro, chloro, bromo and iodo.

The term "aryl" refers to phenyl or substituted phenyl wherein the substituents are selected from lower alkyl, amino, hydroxy, halogeno, thio, alkylthio and arylthio.

The term "heteroaryl" refers to aromatic 4-7 membered rings comprising 1-3 heteroatoms independently selected from oxygen, nitrogen and sulfur. Examples of heteroaryl groups are pyridyl, pyrimidyl, thienyl, furanyl. All positional isomers, e.g. 2-, 3- and 4-pyridyl are included.

Preferred compounds are those wherein Y is $-CH_2-$ or $-O-$. Another group of preferred compounds are those wherein X is $-CH_2-$ or $-CH=$. A preferred group for $R_4$ is $-COOH$, and a preferred group for $R_5$ is $-CH_2COOH$. Other preferred compounds are those wherein $R_9$ and $R_{11}$ are hydrogen and $R_{10}$ is amino. Also preferred are compounds wherein $R_9$ and $R_{11}$ are hydrogen, $R_{10}$ is amino and, $R_8$ is OH, i.e., "B" is guanino. Yet another preferred group is those compounds wherein $R_1$ is hydrogen.

More preferred are compounds wherein X is $-CH_2-$ or $-CH=$, Y is $-O-$ or $-CH_2-$, $R_4$ is $-COOH$ and $R_5$ is $-CH_2COOH$. Also more preferred are compounds wherein X, Y, $R_4$ and $R_5$ are as defined in the preceeding sentence and wherein $R_9$ and $R_{11}$ are hydrogen and $R_{10}$ is amino. A third group is that wherein Y, $R_4$ and $R_5$ have the preferred definitions, X is $-CH_2-$, and $R_1$ is hydrogen.

Typical preferred compounds are those listed in the following table:

| $R_1$ | $R_2$ | X | $R_4$ | $R_5$ | $R^3$ | Y | B |
|---|---|---|---|---|---|---|---|
| H | H | $CH_2$ | COOH | $CH_2COOH$ | H | $CH_2$ | guanino |
| H | H | $CH_2$ | COOH | $CH_2COOH$ | H | O | guanino |
| H | H | $CH_2$ | COOH | $CH_2COOH$ | OH | O | guanino |
| H | H | $CH_2$ | COOH | $CH_2COOH$ | OH | $CH_2$ | guanino |
| Bond | | $CH_2$ | COOH | $CH_2COOH$ | H | $CH_2$ | guanino |
| Bond | | $CH_2$ | COOH | $CH_2COOH$ | OH | $CH_2$ | guanino |
| H | Bond | | COOH | $CH_2COOH$ | H | $CH_2$ | guanino |
| H | Bond | | COOH | $CH_2COOH$ | OH | $CH_2$ | guanino |
| H | Bond | | COOH | $CH_2COOH$ | H | O | guanino |
| H | Bond | | COOH | $CH_2COOH$ | OH | O | guanino |

For those compounds wherein $R^2$ is hydrogen, both the cis and trans isomers are preferred.

The compounds of the invention form salts with various inorganic and organic acids and bases. Such salts include alkali metal salts, e.g. sodium and potassium salts, and alkaline earth metal salts, e.g. calcium and magnesium salts. Salts with organic bases also may be prepared, e.g., N-methylglucamine, lysine and arginine salts. Those compounds with a basic substituent e.g., wherein $R_9$ is hydrogen, may form salts with organic and inorganic acids, e.g., HCl, HBr, $H_2SO_4$, methanesulfonic acid, toluenesulfonic acid, maleic acid, fumaric acid and camphorsulfonic acid. The non-toxic pharmaceutically acceptable salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo, or by exchanging the cations of an existing salt for another cation on a suitable ion exchange resin.

The compounds of the present invention have a number of asymmetric carbon atoms and consequentially various stereoisomers can exist All isomers and racemates are contemplated in the present invention. Examples of stereoisomers of compounds of formula I are as follows:

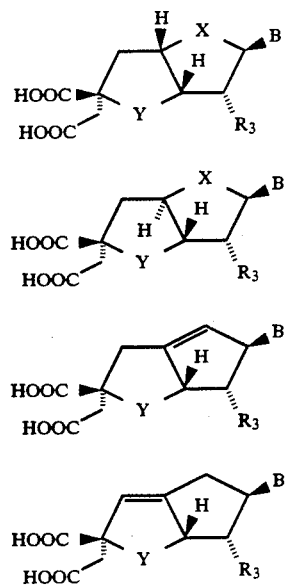

Compounds of the present invention are made by methods well known in the art. For example, a compound of formula Ia is reacted with a compound of formula Ba:

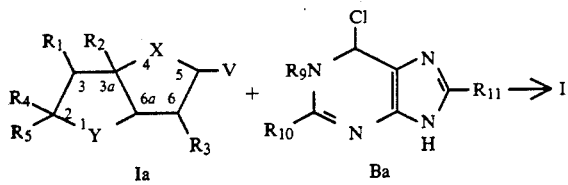

wherein V is a leaving group such as methanesulfonyloxy, tosyl or halogen, with methanesulfonyloxy being preferred. $R_4$, $R_5$ and $R_3$ (when $R_3$ is OH) may be protected by suitable protecting groups, e.g., an alkyl group. The small numbers inside the ring in formula Ia refer to the position of the ring member. Compounds wherein X and Y are —$CH_2$— are octahydropentalenes and compounds wherein X is —$CH_2$— and Y is —O— are hexahydro-2H-cyclopenta[b]furans. Stereochemistry is designated by $\alpha$ or $\beta$.

The reaction is carried out at elevated temperatures (e.g., 60° C.) in an inert solvent such as dimethylformamide in the presence of a base such as potassium carbonate, after which the chloro radical in the "B" portion is displaced with HCl or ammonia to yield the desired $R_8$ substitution.

Compounds of formula Ia can be prepared by several methods, depending on the values of X and Y. For compounds wherein both X and Y are methylene and $R_3$ is hydrogen, a typical procedure is to perform a Knoevenagle reaction with cis-bicyclo[3,3,0]octane-3,7-dione monoketal and cyanoethyl acetate followed by a Michael reaction with cyanide, and to hydrolyze, acidify and reflux the product to obtain the 2,2-diacid. The diacid is then esterified using diazomethane, the isomers are separated and the keto function at the 5-position is stereoselectively reduced using a reagent such as K-selectride ® (potassium tri-sec-butylborohydride, 1 M in tetrahydrofuran) (Aldrich Chemical Co.). The resultant 5-hydroxy group is then mesylated to give a compound of formula Ia wherein $R^4$ is COOMe and $R^5$ is $CH_2COOMe$, i.e. 2$\beta$-methoxycarbonyl-5$\alpha$-methanesulfonyloxy-3$\alpha\beta$, 6$\alpha\beta$-octahydropentalene-2$\alpha$-acetic acid methyl ester.

Compounds of formula Ia wherein X is —CH= and forms a double bond with $R_2$, Y is —$CH_2$ and $R^3$ is hydrogen can be prepared by a modification of the above procedure wherein the $R^2$—X double bond is introduced into the starting material by reacting cis-bicyclo[3,3,0]octane-3,7-dione monoketal with n-butyl lithium and phenylselenyl bromide, followed by treatment with sodium metaperiodate and elimination. The 5-position keto function is then stereoselectively reduced as above and the 2-hydroxy group protected, followed by hydrolysis of the monoketal by mild acid. A Knoevenagle reaction with cyanoethyl acetate is then followed by a Michael reaction with cyanide, acid hydrolysis and decarboxylation to obtain the 2,2-diacid. The diacid is esterified as above, the isomers are separated, the 5-position hydroxy group is deprotected and then mesylated to give a compound such as 2$\beta$-methoxycarbonyl-5$\alpha$-methanesulfonyloxy-1,2,3,6,6$\alpha\beta$-hexahydropentalene-2$\alpha$-acetic acid methyl ester.

For compounds of formula Ia wherein X and Y are methylene and $R^3$ is OH, a typical procedure is to hydrogenate (4S,5R)-o-isopropylidene-3(S)-o-benzoyl-1-hydroxymethyl-1-cyclopentene over palladium/carbon, then to brominate the hydroxy group with carbon tetrabromide and triphenylphosphine. The bromide is displaced with cyanide and the cyanide hydrolized to acid in aqueous methanol and potassium hydroxide. The isopropylidene is then hydrolized in mild acid and lactonized, the hydroxy is protected and an anion of dimethyl-methyl phosphonate is added to the lactone. A Collins oxidation is performed, followed by an intramolecular Wittig reaction. The carbocyclic ring system is hydrogenated with palladium on charcoal and a Knoevenagle reaction is performed on the ketone with cyano-ethyl acetate, followed by a Michael reaction with cyanide, acid hydrolysis and decarboxylation. The resultant 2,2-diacid is esterified with diazomethane, the protecting group at the 5-position is hydrolyzed and then mesylated to give a compound of formula I wherein X and Y are methylene, $R^1$ and $R^2$ are hydrogen, $R^3$ is OH, $R^4$ is COOMe and $R^5$ is —$CH_2COOMe$, i.e. 2$\beta$-methoxycarbonyl-5$\alpha$-methanesulfonyloxy-6$\alpha$-hydroxy-3$\alpha\beta$, 6$\alpha\beta$-octahydropentalene-2$\alpha$-acetic acid methyl ester.

To prepare similar compounds wherein $R^1$ and $R^2$ form a bond, the intermediate lactone described above typically is treated with n-butyl lithium and phenylselenyl bromide and the above procedure continued until the product is esterified. The esterified compound is then treated with sodium metaperiodate, the double bond is introduced, and the above procedure is continued from the deprotection of the 5-position group.

For preparing compounds of formula Ia wherein X is methylene and Y is oxygen, a typical procedure is to add (+)-(5S)-acetoxy-(3R)-hydroxy-cyclopent-1-ene to a solution of ethyl vinyl ether and N-iodosuccinimide, and to cyclize with tri-n-butyltin hydride. The ether group at the 2-position is then alkylated with trimethyl-cyanide/trimethylsilyl-trifluoromethane sulfonate, followed by basic hydrolysis of the cyanide to an acid and esterification with diazomethane. The 5-position hydroxyl group is protected with a group such as t-butyl-dimethylsilyl, and the 2-position is alkylated, e.g., by using iodoethylacetate in the presence of a base. The 5-hydroxy group is deprotected, then mesylated to give a compound of formula Ia wherein X is methylene, Y is oxygen, $R^3$ is hydrogen, $R^4$ is —COOMe and $R^5$ is —$CH_2COOMe$, i.e., 2$\beta$-methoxycarbonyl-5$\alpha$-methanesulfonyl-oxy-3a$\beta$,6a$\beta$-hexahydro-2H-cyclopenta[b]furan-2$\alpha$-acetic acid methyl ester.

For compounds of formula Ia wherein X is —CH= and forms a double bond with $R_2$, and Y is oxygen, a typical reaction procedure is to brominate (4S,5R)-o-isopropylidene-3(S)-o-benzoyl-1-hydroxymethyl-1-cyclopentene with triphenylphosphine/ carbon tetrabromide in an inert solvent such as dimethylformamide. The bromide is then displaced with an anion of diethyl-phenylsulfonylsuccinate and elimination is achieved by refluxing in benzene in the presence of pyridine. The isopropylidene group is hydrolyzed in mild acid and a base-catalyzed Michaels reaction is carried out to effect ring closure The 6-position hydroxy group is protected, the 5-position hydroxy group is deprotected and mesylated to give a compound of formula Ia, e.g., wherein $R^4$ is —COOEt, $R_5$ is —$CH_2COOEt$, $R^3$ is —$OR^{12}$ (wherein $R^{12}$ is a protecting group), X is —CH= and Y is oxygen.

Compounds of formula Ia wherein X is —CH= and forms a double bond with $R_2$, Y is oxygen and $R_3$ is hydrogen may be prepared by deoxygenating the 2$\beta$-methoxycarbonyl-5$\alpha$-o-benzoyl-6$\alpha$-hydroxy-3,5,6,6a$\beta$- tetrahydropentalene-2α-acetic acid methyl ester intermediate prepared in the immediately preceding procedure before removing the benzoyl protecting group at the 5-position. An example of such a compound is 2β-methoxycarbonyl-5α-methanesulfonyloxy-3,5,6,6aβ-tetrahydro-2H-cyclopenta[b]furan-2αacetic acid methyl ester.

Compounds of formula Ia wherein X is —CH$_2$—, R$^1$ and R$^2$ are hydrogen, Y is oxygen and R$^3$ is —OR$^{12}$ can be prepared by using the above procedure wherein X is —CH= and forms a double bond with R$_2$, Y is oxygen and R$^3$ is —OR$^{12}$ after first hydrogenating the cyclopentene starting material.

For preparing compounds of formula Ia wherein X and Y are each —CH$_2$—, R$^3$ is hydrogen and R$^1$ and R$^2$ form a bond, typically cis-bicyclo[3,3,0]octane-3,7-dione monoketal can be reacted with n-butyl lithium and phenylselenyl bromide, followed by a Knoevenagle reaction with cyanoethyl acetate and a Michael reaction with cyanide. The reaction product is then hydrolyzed, acidified and refluxed to obtain the 2,2-diacid. The diacid can then be esterified with diazomethane, the product treated with sodium metaperiodate, the R$^1$—R$^2$ double bond is effected and the isomers separated. The keto function can be stereoselectively reduced and the hydroxy group mesylated as described above to prepare a compound such as 2β-methoxycarbonyl-5α-methanesulfonyloxy-1,2,4,5,6,6aβ-hexahydropentalene-2α-acetic acid methyl ester.

The above typical procedures yield cis-octahydropentalenes or cis-hexahydro-2H-cyclopenta[b]furans. To obtain the corresponding trans isomers, catalytic hydrogenation of the corresponding unsaturated compound (i.e. wherein R$_1$ and R$_2$ form a double bond or wherein X is —CH=, and R$_2$ and X form a double bond) can be performed, e.g. an alcoholic solution of the unsaturated compound with a catalytic amount of Pd/C is hydrogenated at 60 psi until the reaction is complete, the resultant residue is filtered and the solvent is evaporated to give the desired compound.

Analogous starting materials and procedures may be used to prepare compounds wherein X is NH or P and Y is NH, S or P.

Following are examples of the preparation of compounds of this invention.

EXAMPLE 1

5-α-R-(2-AMINO-1,6-DIHYDRO-6-OXO-9H-PURIN-9-YL)-2β-CARBOXYOCTAHYDRO-2α-PENTALENEACETIC ACID

STEP 1

Combine cis-bicyclo[3,3,0]octane-3,7-dione monoketal (1 mmol), cyanoethylacetate (1.2 eq), acetic acid (0.8 eq) and ammonia acetate (0.1 to 0.3 mmol) in benzene (15 ml) and reflux for 3 hours. Dilute the resultant reaction mixture with benzene (50 mL), extract with saturated sodium bicarbonate solution, dry the organic layer over magnesium sulfate and evaporate the solvent.

STEP 2

Treat the product of Step 1 (1.0 mmol in 10 ml aqueous ethanol) with potassium cyanide (2.0 mmol) at room temperature for ½hour. Adjust the resultant solution to pH 5 with 1 N HCl, evaporate the solvent, and reflux the resultant residue in 6 N HCl (25 ml) for 16 hours. Evaporate the hydrochloric acid under high vacuum, dissolve the resultant residue in ethylacetate, wash with 10% sodium bicarbonate solution and evaporate the ethylacetate. Dissolve the resultant residue in tetrahydrofuran (THF) (20 mL) and cool in an ice bath. Add diazomethane until the reaction is complete as monitored by thin layer chromatography (TLC). Neutralize the excess diazomethane with acetic acid. Chromatograph the resultant residue on a silica gel column eluted with diethylether:benzene (3:1) to obtain the title compound as a mixture of isomers. Chromatograph (TLC) on silica gel with 30% diethylether in benzene as eluent to give an R$_f$ of 0.7. NMR (400 Hz): δ1.4 (2H,dd,J=7.5 and 14.0 Hz); 2.10 (2H,dd,J=4.0 Hz, 16.0 Hz); 2.4-2.7 (4H,m); 2.75 (S,2H), 2.95 (m,1H); 3.65 and 3.75 (2S, 6H).

STEP 3

Cool a solution of the product of Step 2 (1.0 mmol) in THF (20 mL) to −78° C., add K-Selectride® (1.2 mmol), warm the mixture to room temperature and stir for ½hour. Add saturated NH$_4$Cl (5 ml) and concentrate in vacuo. Dissolve the residue in CH$_2$Cl$_2$ and wash with water. Dry the organic layer over MgSO$_4$ and concentrate in vacuo. Chromatograph (TLC) on silica gel eluting with 50% ethylacetate in petroleum ether to give an R$_f$ of 0.50. NMR (200 MHz): δ1.6-1.7 (4H,m); 1.7-2.1 (2H,m); 2.4-2.7 (4H,m); 2.75 (2H,s,CH$_2$COOMe); 3.65 and 3.75 (6H, 2S, OCH$_3$); 4.4 (1H,m).

STEP 4

Cool a solution of the product of Step 3 (1.0 mmol) and triethylamine (1.2 mmol) in methylene chloride (10 mL) in an ice bath. Add methane sulfonylchloride (1.2 mmol) and stir at room temperature for 2 hours. Dilute the resultant mixture with methylene chloride (50 mL), wash with water, then saturated sodium bicarbonate solution, dry the organic layer over magnesium sulfate and evaporate the solvent. Perform TLC on silica gel, eluting with 50% ethyl acetate in petroleum ether to give a R$_f$ of 0.7. NMR (200 MHz): δ1.25 (1H,dd,J,6.0 Hz); 1.85 (1H,dd,J=14.0 Hz); 2.15 (3H,m); 2.6 (2H,m); 2.75 (2H,S, CH$_2$COOMe); 2.8 (1H,m); 3.05

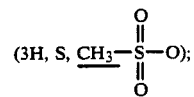

(3H, S, $CH_3$—$\overset{\overset{O}{\|}}{\underset{\underset{O}{\|}}{S}}$—O);

3.65 and 3.75 (6H,2S, 2 OCH$_3$); 5.2 (1H,m).

STEP 5

Combine the product of Step 4 (1.0 mmol), 2-amino-6-chloropurine (1.2 mmol) and potassium carbonate (1.2 mmol) in dimethylformamide (5 ml) and maintain at 60° C. for 16-24 hours. Evaporate the solvent and partition the resultant residue between water and methylene chloride. Separate the organic layer, dry over MgSO$_4$ and evaporate to dryness. Chromatograph the resultant residue on silica gel, eluting with 50% ethyl acetate in petroleum ether. Perform TLC on silica gel, eluting with 60% ethylacetate:40% petroleum ether to give an R$_f$ of 0.25. NMR (200 Hz): δ7.95 (S,1H); 5.2 (6S,2H,NH$_2$); 4.7 (m,1H); 3.6-5.7 (2S,6H,2OCH$_3$); 2.9 (S,2H,CH$_2$COOCH$_3$); 2.4-2.8(4H,m); 2.1-2.2 (2H,m); 1.5(dd,2H).

STEP 6

Stir the product of Step 5 (1.0 mmol) and sodium hydroxide (5 mmol) in aqueous ethanol (10 ml) for 4 hours. Neutralize with 1 N HCl and evaporate the solvent. Dissolve the resultant residue in 1 N HCl (10 ml) and reflux for 12-16 hours, until high pressure liquid chromatography (HPLC) shows reaction is complete. Adjust the resultant solution to pH 4 and reduce solvent volume to half. Charge the solution to a CHP$_{20}$P gel (Mitsubishi Chemical Industries) column and elute with water, followed by 50% acetone in water. Mass Spectrum M+1=362.

Using the appropriate starting materials one also could produce 5$-R-(2-amino-1,6-dihydro-6-oxo-9H-purin-9-yl)-2αcarboxyoctahydro-2β-pentaleneacetic acid.

EXAMPLE 2

5β-R-(2-AMINO-1,6-DIHYDRO-6-OXO-9H-PURIN-9-YL)-2-βCARBOXYHEXAHYDRO-2H-CYCLOPENTA[b]FURAN-2α-ACETIC ACID

STEP 1

To a solution of (+)-(5S)-acetoxy-(3R)-hydroxy-cyclopent-1-ene (1 mmol) and N-iodo-succinimide (1 mmol) in dichloromethane (30 ml) at −20° C., add ethylvinyl ether (1.0 mmol) dropwise and maintain reaction at −20° C. for 4 hours. Wash the reaction mixture with water, dry and concentrate. Chromatography (TLC), eluting with 20% ethyl acetate in petroleum ether, gives a R$_f$=0.75. NMR (200 MHz): δ1.25 (3H,t,OCH$_2$CH$_3$); 2.1

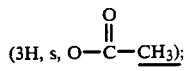

2.85 (1H,m,H-4); 3.25 (2H, Abq, CH$_2$I); 3.7 (2H, OCH$_2$CH$_3$); 4.65 (1H,m,H-3); 4.7 (1H,m); 5.5 (bt, 1H, H-5); 6.0–6.15 (2m,2H,H-1, H-2).

STEP 2

To a refluxing solution of the product of Step 1 (1.0 mmol) in benzene (100 mL), add a solution of tri-n-butyltin hydride (1.2 mmol) in benzene (100 mL) over a period of 4 hours. Wash the resultant mixture with water, dry and concentrate. Column chromatograph the resultant residue on flash silica gel using 10% ethyl acetate in petroleum ether as eluent. TLC using 10% ethyl acetate in petroleum ether as eluent gave an R$_f$ of 0.78. NMR (200 MHz): δ1.2 (3H,t,OCH$_2$CH$_3$); 1.75 (bdt, 1H); 1.8–2.3 (m,5H); 2.1 and 2.15

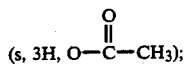

2.8 (m,1H); 3.45. and 3.75 (m,2H,OCH$_2$CH$_3$); 4.65 (m,1H,H-1); 5.114 5.3 (2m,2H,H-7, H-3).

STEP 3

Cool a solution of the product of Step 2 (1.0 mmol) in CH$_2$Cl$_2$ (50 mL) to −78° C., add a catalytic amount of trimethylsilyl-trifluoro methane sulfonate and trimethylsilylcyanide (1.2 mmol). Warm the reaction to −40° C. and keep at that temperature for 2 hours. Wash the resultant mixture with a saturated solution of sodium bicarbonate, dry and concentrate. Perform TLC on the resultant residue, eluting with 40% ethyl acetate in pet ether to give an R$_f$=0.70. NMR (200 MHz): δ1.8 (bd,1H); 2.0–2.3 (m,4H); 2.5 (dt,1H); 3.0 (m,1H,H-5); 4.85 (dt,1H,H-7); 4.9 (dd,1H,H-1); 5.2 (m,1H,H-3).

STEP 4

Reflux a solution of the product of Step 3 (1.0 mmol) in aqueous ethanol for 1 hour with potassium hydroxide. Acidify to pH 6 and extract with methylene chloride, dry and concentrate. Dissolve the residue in diethyl ether, treat with diazomethane, and concentrate the reaction mixture. Perform TLC, eluting with 5% methanol in methylene chloride to give an R$_f$=0.35. NMR (200 MHz): δ1.7 (bd,1H); 1.9–2.4 (m,5H); 2.8 (m,1H,H-5); 3.75

4.3 (m,1H,H-7); 4.7–4.85 (m,2H,H-1, H-3).

STEP 5

Cool a solution of the product of Step 4 (1.0 mmol) in THF (20 mL) to −78°, add lithium diisopropyl amide (2.2 mmol) and keep at −78° for ½hour. Add iodoethyl acetate (2.2 mmol) and slowly warm the reaction mixture. Add a solution of saturated ammonium chloride, concentrate, and dissolve the residue in CH$_2$Cl$_2$. Wash with water, dry the organic layer and concentrate. Chromatograph the resultant residue a column of flash silica gel, eluting with 5% methanol in methylene chloride. Separate the two isomers by TLC, eluting with 5% methanol in methylene chloride to give an R$_f$=0.40 for the desired compound. NMR (200 MHz): δ1.3 (3H,t,OCH$_2$CH$_3$); 1.8 (2H,m); 2.2–2.6 (m,4H); 2.8 (m,1H); 2.75 and 3.05 (2H, JAB=15.0,

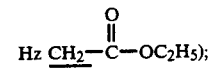

3.85 (3H,sOCH$_3$; 4.2 (2H,q,OCH$_2$CH$_3$); 4.25 (1H,m,H-7); 4.6 (1H,t,H-1).

STEP 6

Treat the product of Step 5 as described in Steps 4–6 of Example 1 to obtain the title compound. NMR (200 MHz): δ2.1 (2H,m), 2.3–2.75 (4H,m), 2.9 (2H, ABq, JAB=15.0, Hz),

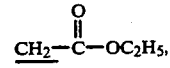

7.95 (s,1H). Mass spectrum M+1=364.

Using the appropriate starting materials one also could produce 5β-R-(2-amino-1,6-dihydro-6-oxo-9H-purin-9-yl)-2α-carboxyhexahydro-2H-cyclopenta[b]furan-2β-acetic acid.

EXAMPLE 3

5β-R-(2-AMINO-1,6-DIHYDRO-6-OXO-9H-PURIN-9-YL)-2β-CARBOXYHEXAHYDRO-6-HYDROXY-2H-CYCLOPENTA[b]FURAN-2α-ACETIC ACID

STEP 1

Hydrogenate a solution of (4S,5R)-o-iso-propylidene-3(S)-o-benzoyl-1-hydroxymethyl-1-cyclopentene (1.0 mmole) in absolute ethanol (50 mL) with Palladium/- carbon until TLC shows completion of the reaction. Filter the resultant solution and remove the solvent under reduced pressure.

STEP 2

Treat a solution of the product of Step 1 (1.0 mmole) in dimethylformamide (DMF) (10 mL) with triphenyl phosphine (1.2 mmole) and carbontetrabromide (1.2 mmole) until reaction is complete by TLC. Remove the solvent and column chromatograph the resultant residue on silica gel using 50% ethyl acetate in petroleum ether as eluent.

STEP 3

Cool a solution of diethylphenyl-sulfonyl succinate (1.2 mmole) in THF (20 mL) to −78°, add lithium diisopropylamide (1.2 mmole) and keep at −78° for ½hr. Add the product of Step 2 (1.0 mmole) and slowly warm the reaction mixture to room temperature. Add a solution of saturated ammonium chloride, concentrate and dissolve the residue in $CH_2Cl_2$, wash with water, dry the organic layer and concentrate. Dissolve the resultant residue in benzene (50 mL), add pyridine (2.0 mmole) and reflux the resulting solution until elimination is complete (2 to 4 hrs.). Remove the solvent to give the crude product, which is used in the next step without any purification.

STEP 4

Dissolve the product of Step 3 (1.0 mole) in dioxane, add 1 N HCl and stir the reaction mixture at room temperature for several hours (3 to 6 hrs.). Neutralize the reaction mixture, evaporate the solvent, dissolve the resultant residue in methylene chloride, wash with water, dry and evaporate the solvent. Purify the product on a column of silica gel using ethyl acetate as a eluent.

STEP 5

Treat a solution of the product of Step 4 (1.0 mmole) in dry THF with a base such as sodium hydride or lithium diisopropyl amide (2.2 mmole) and stir the reaction mixture at room temperature. Monitor the reaction by TLC. At the completion of the reaction, neutralize the mixture and concentrate the solvent. Dissolve the residue in an organic solvent, wash with water, dry, and evaporate the solvent. Dissolve the crude product in dry DMF and treat with imidazole (1.2 mole) and t-butyl dimethyl silyl chloride (1.2 mmole) at elevated temperature (80° C.) until the reaction is complete. Pour the reaction mixture into ice/water, extract with $CH_2Cl_2$, wash with water, dry and evaporate the solvent to give a crude product. Separate the isomers and isolate the desired product.

STEP 6

Treat a solution of the product of Step 5 (1.0 mmol) in absolute ethanol with sodium ethoxide (1.2 mmole) for several hours. Neutralize the reaction mixture and remove the solvent. Dissolve the resultant residue in methylene chloride, wash with water, dry over sodium sulfate and evaporate the solvent. Dissolve the crude product in methylene chloride and treat with methane sulfonylchloride and triethylamine as described in Step 4 of Example 1. Dilute the resultant reaction mixture with $CH_2Cl_2$ and wash with water followed by a 10% solution of sodium bicarbonate, dry and evaporate the solvent. Purify the crude product on a column of silica gel using 50% ethyl acetate in petroleum ether as eluent.

STEP 7

Treat the product of Step 6 as described in Steps 5–6 of Example 1 to obtain the title compound.

EXAMPLE 4

5β-R-(2-AMINO-1,6-DIHYDRO-6-OXO-9H-PURIN-9-YL)-2βCARBOXYOCTAHYDRO-6α-HYDROXY-2α-PENTALENEACETIC ACID

STEP 1

Treat a solution of the product of Step 2 in Example 3 (1.0 mmol)·in DMF with potassium cyanide (1.2 mmol) at elevated temperature (100–120°) until the reaction is complete. Pour the reaction mixture into an ice bath, extract with methylene chloride, wash with water, dry and evaporate the solvent. Convert the crude product to the ester as described in Step 4 of Example 2.

STEP 2

Hydrolyze the isopropylidene group of the product of Step 1 as described in Step 4 of Example 3. Dissolve the resultant residue in benzene and reflux with a catalytic amount of p-toluenesulfonic acid. Wash the resultant residue with a saturated solution of sodium bicarbonate and remove the solvent. Dissolve the residue in DMF, add t-butyldimethylsilyl chloride (1.2 mmole) and imidazole (1.2 mmole) and keep the reaction mixture at elevated temperature until reaction is complete (4–8 hrs.). Pour the reaction mixture on an ice/water mixture, extract the product with methylene chloride, dry the organic layer and evaporate the solvent.

STEP 3

Convert the lactone from Step 2 to an α-β unsaturated ketone using the procedure described in Steps 2 and 3 of Example 6.

STEP 4

Dissolve the product from Step 3 in absolute ethanol and hydrogenate with palladium on carbon. Filter the resultant solution and evaporate the solvent.

STEP 5

Convert the ketone from Step 4 to the diester using the procedure described in Steps 1 and 2 of Example 1. Hydrolyze the product according to the procedure described in Step 6 of Example 3, using methanol and sodium methoxide instead of ethanol and sodium-ethoxide.

STEP 6

Mesylate the product of Step 5 using the procedure of Step 4 of Example 1. Continue with the procedures described in Steps 5 and 6 of Example 1 to obtain the title compound.

EXAMPLE 5

5β-R-(2-AMINO-1,6-DIHYDRO-6-OXO-9H-9-YL)-2β-CARBOXY-1,2,4,5,6,6aβ-HEXAHYDRO-2α-PENTALENEACETIC ACID

STEP 1

Cool a solution of cis-bicyclo[3,3,0]-octane-3,7-dione (1.0 mmole) in dry THF (15 mL) to −78°, add lithium-diisopropylamide (1.2 mmol) and keep at −78° for ½ hour. Add phenylseleneyl bromide and slowly warm the reaction mixture. Add a saturated solution of ammonium chloride, concentrate, dissolve the resultant residue in methylene chloride, wash with water, dry the organic layer and concentrate.

Treat the resultant crude product in the manner described in Steps 1 and 2 of Example 1.

STEP 2

Dissolve the product of Step 1 in dichloroethane and oxidize with sodium metaperiodate. Dilute the reaction mixture, wash with water, dry and evaporate the solvent. Redissolve the crude mixture in a high boiling solvent and reflux until elimination is complete. Remove the solvent and purify the crude product on silica gel.

STEP 3

Treat the product of Step 2 in the manner described in Steps 3–5 of Example 1 to obtain the title compound.

EXAMPLE 6

5β-R-(2-AMINO-1,6-DIHYDRO-6-OXO-9H-PURIN-9-YL)-2β-CARBOXY-1,2,4,5,6,6aβ-HEXAHYDRO-6α-HYDROXY-2α-PENTALENEACETIC ACID

Step 1

Treat the product from Step 2 of Example 4 in the manner described in the first paragraph of Step 1 of Example 5.

STEP 2

Cool a solution of dimethyl methylphosphonate (2.0 mmol) in dry THF (25 mL) to −78°, add n-butyl lithium (2.0 mmole) and keep at −78° for 15 minutes. Add the product of Step 1 and warm the reaction mixture slowly. Add a saturated solution of ammonium chloride, concentrate, dissolve the residue in $CH_2Cl_2$, wash with water, dry the organic layer and concentrate. Purify the crude product on a silica gel column using 50% ethyl acetate in petroleum ether as the eluant.

STEP 3

Cool a solution of pyridine (12.0 mmole) in methylene chloride (75.0 mL) in an ice bath. Add chromium trioxide (6.0 mmole) and stir the reaction for 15 minutes. Add a solution of product from Step 2 in methylene chloride and stir the reaction mixture until oxidation is complete. Dilute the reaction mixture with diethyl ether (100 mL), filter through a pad of florisil and concentrate. Dissolve the crude product in dry benzene (100 mL for each 1.0 mmol). Add powdered anhydrous potassium carbonate (1.2 mmol) and 18 crown-6 (0.5 mmole) and reflux the reaction mixture until reaction is complete. Filter and concentrate the reaction mixture.

STEP 4

Hydrogenate a solution of the product from Step 3 in ethanol in the presence of palladium/carbon. Filter and concentrate the reaction mixture and treat the resultant residue as described in Steps 1 and 2 of Example 1.

STEP 5

Treat the product of Step 4 as described in Step 2 of Example 5 and separate the isomers on silica gel.

STEP 6

Treat the product of Step 5 as described in Step 6 of Example 3, using methanol and sodium methoxide in place of ethanol and sodium ethoxide. Prepare the title compound by treating the crude product as described in Steps 4–6 of Example 1.

EXAMPLE 7

5β-R-(2-AMINO-1,6-DIHYDRO-6-OXO-9H-PURIN-9-YL)-2β-CARBOXY-1,2,3,4,5,6,6aβ-HEXAHYDRO-2α-PENTALENEACETIC ACID

STEP 1

Cool a solution of the product of Step 2 of Example 5 (1.0 mmole) in THF (20 mL) to −78°. Add K-selectride ® (1.2 mmole), warm the mixture to room temperature and stir for ½ hour. Add saturated $NH_4Cl$ solution, concentrate, dissolve the residue in methylene chloride and wash with water. Dry and concentrate the organic layer. Dissolve the crude product (1.0 mmole) in methylene chloride and treat with t-butyldimethylsilyl chloride (1.2 mmole) and imidazole (1.2 mmole) at room temperature. After completion of reaction, dilute the reaction mixture with methylene chloride, wash with water, dry and concentrate.

STEP 2

Dissolve the product of Step 1 in aqueous acetic acid and stir at room temperature for 6–8 hours. Neutralize the reaction mixture and evaporate the solvent.

STEP 3

Treat the product of Step 2 as described in Steps 1, 2, 4, 5 and 6 of Example 1 to obtain the title compound.

EXAMPLE 8

5β-R-(2-AMINO-1,6-DIHYDRO-6-OXO-9H-PURIN-9-YL-2β-CARBOXY-3,5,6,6aβ-TETRAHYDRO-6α-HYDROXY-2H-CYCLOPENTA[b]FURAN-2α-ACETIC ACID

STEP 1

Convert (4S,5R)-o-isopropylidene-3(S)-o-benzoyl-1-hydroxymethyl-1-cyclopentene to the bromide using the procedure described in Step 2 of Example 3.

STEP 2

1 Treat the product of Step 1 as described in Steps 3 and 4 of Example 3.

STEP 3

Treat a solution of product of Step 2 (1.0 mmole) in THF with base (1.0 mmole) and stir at room temperature, monitoring by TLC. At the completion of the reaction, neutralize and concentrate the reaction mixture. Dissolve the resultant residue in methylene chloride, wash with water, dry the organic layer and remove the solvent.

STEP 4

Treat the product of Step 3 using the procedure described in Steps 5 to 7 of Example 3 to obtain the title compound.

EXAMPLE 9

5β-R-(2-AMINO-1,6-DIHYDRO-6-OXO-9H-PURIN-9-YL)-2β-CARBOXY-3,5,6,6aβ-TETRAHYDRO-2H-CYCLOPENTA[b]FURAN-2α-ACETIC ACID

STEP 1

Treat a solution of the product of Step 3 of Example 8 (1.0 mmole) in dry THF (30 mL) with oil free sodium hydride (1.2 mmole). Add carbon disulfide (1.2 mmole) and reflux the reaction mixture. Cool the solution, add methyl iodide (1.2 mmole), and reflux for 4–7 hours. Add water, evaporate the solvent, dissolve the residue in methylene chloride, wash with 5% HCl, saturated sodium bicarbonate and water, dry and evaporate the solvent. Dissolve the resultant residue in toluene or xylene (50 mL) and reflux. Slowly add a solution of tri-n-butyltin hydride in toluene or xylene and reflux the resulting solution overnight. Evaporate the solvent and purify the resulting residue on a silica gel column using 5% ethyl acetate in petroleum ether as the eluant.

STEP 2

React the product of Step 1 in the manner described in Steps 6 and 7 of Example 3 to obtain the title compound.

EXAMPLE 10

2α-CARBOXYHEXAHYDRO-6β-HYDROXY-5β-R-(6-HYDROXY-9H-PURIN-9-YL)-2H-CYCLOPENTA[b]FURAN-2α-ACETIC ACID

STEP 1

Cool a solution of the product of Step 5 of Example 2 (1.0 mmol) and triethylamine (1.2 mmol) in methylene chloride (10 mL) in an ice bath. Add methane-sulfonyl chloride (1.2 mmol) and stir at room temperature for 2 hours. Dilute the resultant mixture with methylene chloride (50 mL), wash with water, and a saturated sodium bicarbonate solution, dry the organic layer over magnesium sulfate and evaporate the solvent. Perform the TLC on silica gel, eluting with ethylacetate to give an $R_f$ of 0.65; NMR (200 MHz); $\delta$1.28 (3H,t,OCH$_2$CH$_3$). 2.15 (2H,m), 2.85 (2H, JAB=15.5,

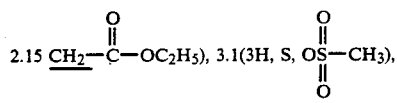

3.85 (3H,S,OCH$_3$) 4.15, 4.3 (2H, qOCH$_2$CH$_3$)

STEP 2

Combine the product of Step 1 (1.0 mmol), 6-chloropurine (1.2 mmol) and potassium carbonate (1.2 mmol) in dry dimethylformamide (5 mL) and treat it as described in Steps 5 and 6 of Example 1 to produce title 2.8 (2H, ABq, JAB=1.5 Hz,

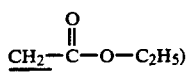

5.1 (1H,m) 7.95 & 8.1 (2×1H, s). Mass spectrum M+1=349.

The compounds of the present invention can also be prepared by another route using compounds of formula Ib,

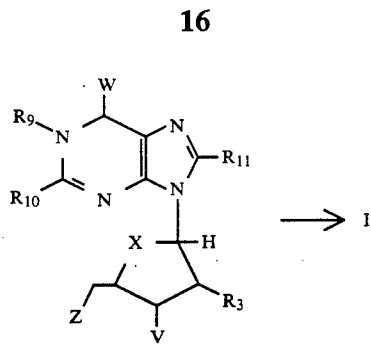

which already contains base B where Z is

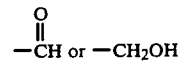

and V is CH$_2$OR, OR, SR or NR where R is a protecting group. Using methods well known in organic synthesis, Z and V functionally can be modified and cyclized to produce I.

EXAMPLE 11

2α-CARBOXYHEXAHYDRO-6β-HYDROXY-5β-R-(6-HYDROXY-9H-PURIN-9-YL)-2H-CYCLOPENTA[b]FURAN-2α-ACETIC ACID

STEP 1

Hydrogenate a solution of (4S,5R)-O-isopropylidene-3(S)-O-benzoyl 1-hydroxy-methyl-1-cyclopentene (1.0 mmol) in absolute ethanol (50 mL) with palladium on carbon until the reaction is complete. Filter the resultant solution and remove the solvent under reduced pressure.

STEP 2

Treat a solution of the product of Step 1 (1.0 mmol) in dry pyridine (50 mL) with triphenyl-methyl chloride (1.1 mmol) overnight. Pour the reaction mixture in ice water, decant the liquid and redissolve the residue in methylene chloride and wash with 10% hydrochloric acid, water and saturated sodium bicarbonate solution. Dry the organic layer over magnesium sulfate, remove the solvent under reduced pressure and azeotrope with toluene.

STEP 3

Treat a solution of the product of Step 2 (1.0 mmol) in methanol (100 mL) with sodium-methoxide until TLC shows completion of the reaction. Neutralize the reaction and remove the solvent. Dissolve the residue in methylene chloride, wash with water, dry and concentrate.

STEP 4

Treat the product of Step 3 as described in (1.0 mmol) with 6-chloropurine (1.2 mmol) and potassium e (1.2 mmol) in dimethylformamide (5 mL) and maintain at 60° for 16–24 hours. Evaporate the solvent and partition the resultant residue between water and methylene chloride. Dry the organic layer and concentrate. Chromatograph the residue on silica gel.

STEP 5

Dissolve the product of Step 4 (1.0 mmol) in dry methylene chloride (100 mL) and cool to −78°. Add diethylaluminum iodide (4.0 mmol) to it. After ½hour, pour the reaction mixture into an ice cold solution of sodium bicarbonate. Separate the organic layer, dry and concentrate. Chromatograph the residue on silica gel.

STEP 6

Treat the product of Step 5 as described in Steps 2-4 of Example 3.

STEP 7

Treat a solution of the product to Step 6 (1.0 mmol) in dry tetrahydrofuran with a base such as sodium hydride or lithium diisopropylamide (2.2 mmol) and stir the reaction mixture at room temperature. Monitor the reaction by TLC. At the completion of the reaction, neutralize the mixture and concentrate the solvent. Column chromatograph the residue on silica gel.

STEP 8

Treat the product of Step 7 as described in Step 6 of Example 1 to obtain the title compound of Example 11.

The compounds of this invention are useful in view of their pharmacological properties. In particular, compounds of this invention possess activity as anti-hypertensive agents.

The compounds of this invention can be combined with pharmaceutical carriers to prepare well known pharmaceutical dosage forms suitable for oral or parenteral administration. Such pharmaceutical compositions are useful in the treatment of cardiovascular disorders and particularly mammalian hypertension.

The effective daily antihypertensive dose of the compounds of this invention will typically be in the range of about 1-50, preferably about 1-25, mg/kg mammalian weight, administered in single or divided doses. The exact dose to be administered is determined by the attending clinician and is dependent upon where the particular compound lies within the above quoted range, as well as upon the age, weight and condition of the individual.

Generally, in treating humans having hypertension, the compounds of this invention may be administered to patients in need of such treatment in a dosage range of about 10 to about 300 mg per patient generally given several (e.g., 1-4) times a day, thus giving a total daily dosage of from about 10 to about 1200 mg per day. The compounds are believed to be non-toxic within the recommended dosage range.

The compounds of the present invention are preferably administered orally, e.g., in tablets or capsule form, but may also be administered parenterally, e.g., injectable solutions or suspensions. Also contemplated are mechanical delivery systems, e.g., transdermal dosage forms.

I claim:

1. Compounds represented by the formula

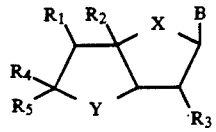
I $R_1$ is hydrogen or $R_1$ and $R_2$ together form a double bond;

$R_2$ is hydrogen or $R_2$ may form a double bond with either $R_1$ or X;

$R_3$ is hydrogen or OH;

$R_4$ is hydrogen or $-(CH_2)_n COOR_6$;

$R_5$ is $R_4$ or $-CH(COOR_6)(CH_2COOR_6)$, provided that $R_4$ and $R_5$ are not both hydrogen;

$R_6$ is hydrogen or lower alkyl;

n is 0-4;

X is $-CH_2-$ or when $R_1$ is hydrogen, X may be $-CH=$ and form a double bond with $R_2$;

Y is $-CH_2-$ or $-O-$;

B is

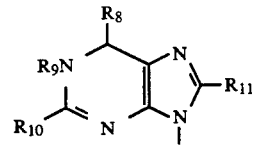

$R_8$ $-OH$ or $-NH_2$;

$R_9$ is hydrogen, lower alkyl or aryl;

$R_{10}$ is hydrogen, amino, lower alkylamino, arylamino, or lower alkylcarbonylamino;

$R_{11}$ is hydrogen, halogeno, lower alkyl or aryl; and the pharmaceutically acceptable esters or salts thereof.

2. The compound of claim 1 further characterized by:

$R_1$ and $R_2$ each being hydrogen or $R_1$ and $R_2$ together forming a double bond;

$R_3$ being hydrogen or OH;

$R_4$ and $R_5$ are both $(CH_2)_n COOH$;

n is 0 or 1;

X is $-CH_2-$ or when $R_1$ is hydrogen, X may be $-CH=$ and form a double bond with $R_2$; and Y is $-CH_2-$ or oxygen.

3. The compound of claim 2 further characterized by:

$R_8$ being OH or $NH_2$;

$R_9$ being hydrogen;

$R_{10}$ being OH or $NH_2$; and $R_{11}$ being hydrogen.

4. A compound of claim 1 named:

5β-R-(2-amino-1,6-dihydro-6-oxo-9H-purin-9-yl)-2β-carboxyoctahydro-2α-pentaleneacetic acid;

5β-R-(2-amino-1,6-dihydro-6-oxo-9H-purin-9-yl)-5β-carboxyhexahydro-2H-cyclopenta[b]furan-2α-acetic acid;

5β-R-(2-amino-1,6-dihydro-6-oxo-9H-purin-9-yl)-2β-carboxyhexahydro-6-hydroxy-2H-cyclopenta[b]furan-2α-acetic acid;

5α-R-(2-amino-1,6-dihydro-6-oxo-9H-purin-9-yl)-2β-carboxyoctahydro-6α-hydroxy-2α-pentaleneacetic acid;

5β-R-(2-amino-1,6-dihydro-6-oxo-9H-purin-9-yl)-2β-carboxy-1,2,4,5,6,6aβ-hexahydro-2α-pentaleneacetic acid;

5β-R-(2-amino-1,6-dihydro-6-oxo-9H-purin-9-yl)-2β-carboxy-1,2,4,5,6,6aβ-hexahydro-6-hydroxy-2α-pentaleneacetic acid;

5β-R-(2-amino-1,6-dihydro-6-oxo-9H-purin-9-yl)-2β-carboxy-1,2,3,5,6,6aβ-hexahydro-2α-pentaleneacetic acid;

5β-R-(2-amino-1,6-dihydro-6-oxo-9H-purin-9-yl)-2β-carboxy-3,5,6,6aβ-tetrahydro-6-hydroxy-2H-cyclopenta[b]furan-2α-acetic acid;

5β-R-(2-amino-1,6-dihydro-6-oxo-9H-purin-9-yl)-2β-carboxy-3,5,6,6aβ-tetrahydro-2H-cyclopenta[b]furan-2α-acetic acid;

2α-carboxyhexahydro-6β-hydroxy-5β-R-(6-hydroxy-9H-purin-9-yl)-2H-cyclopenta[b]furan-2α-acetic acid;

5β-R-(2-amino-1,6-dihydro-6-oxo-9H-purin-9-yl)-2α-carboxyoctahydro-2β-pentaleneacetic acid; or 5β-R-(2-amino-1,6-dihydro-6-oxo-9H-purin-9-yl)-2αcarboxyoctahydro-2H-cyclopenta[b]furan-2β-acetic acid.

5. A compound as defined in claim 1 in combination with a pharmaceutically acceptable carrier.

6. A method for reducing blood pressure in hypertensive mammals comprising administering to a mammal in need of such treatment an effective amount of a compound of claim 1 in combination with a pharmaceutically acceptable carrier.

* * * * *